US009279026B2

(12) United States Patent
Fields et al.

(10) Patent No.: US 9,279,026 B2
(45) Date of Patent: Mar. 8, 2016

(54) POLYACETYLENE AND CHLORINATED POLYACETYLENE AND PRODUCTION PROCESSES THEREOF

(71) Applicant: Lubrizol Advanced Materials, Inc., Cleveland, OH (US)

(72) Inventors: Garry L. Fields, Richfield, OH (US); James D. Burrington, Gates Mills, OH (US); Andrew M. Olah, Spencer, OH (US)

(73) Assignee: Lubrizol Advanced Materials, Inc., Cleveland, OH (US)

( * ) Notice: Subject to any disclaimer, the term of this patent is extended or adjusted under 35 U.S.C. 154(b) by 51 days.

(21) Appl. No.: 14/352,324

(22) PCT Filed: Oct. 15, 2012

(86) PCT No.: PCT/US2012/060204
§ 371 (c)(1),
(2) Date: Apr. 17, 2014

(87) PCT Pub. No.: WO2013/059109
PCT Pub. Date: Apr. 25, 2013

(65) Prior Publication Data
US 2014/0288243 A1     Sep. 25, 2014

Related U.S. Application Data

(60) Provisional application No. 61/549,370, filed on Oct. 20, 2011.

(51) Int. Cl.
*C08F 138/02* (2006.01)
*C08F 8/20* (2006.01)
*C08F 38/02* (2006.01)
*C08F 238/02* (2006.01)
*C08F 8/22* (2006.01)

(52) U.S. Cl.
CPC .................. *C08F 138/02* (2013.01); *C08F 8/20* (2013.01); *C08F 8/22* (2013.01); *C08F 38/02* (2013.01); *C08F 238/02* (2013.01)

(58) Field of Classification Search
None
See application file for complete search history.

(56) References Cited

U.S. PATENT DOCUMENTS 3,367,925 A     2/1968 Liu et al.
4,579,921 A *   4/1986 Gouarderes et al. ........... 526/159
4,834,911 A *   5/1989 Carew ........................... 252/500

OTHER PUBLICATIONS

Akagi, International Journal of Quantum Chemistry: Quantum Chemistry Symposium 24, 041-050 (1990).*

(Continued)

*Primary Examiner* — Robert C Boyle
(74) *Attorney, Agent, or Firm* — Christopher P. Demas; Teresan W. Gilbert

(57) ABSTRACT

The present invention is directed to a heterogeneous gas phase polymerization process to produce true polyacetylene (PA; $C_2H_2$) in powder form, and the resultant PA product. The present invention is additionally directed to a chlorinated polyacetylene (CPA) compound comprised of primarily CHCl units and CH double bond units. The CPA compound can be comprised of at least 67.3 wt % Cl, and have a weight average molecular weight (Mw) as measured by GPC of greater than 30,000 and contain less than 1.0 mol % carbon-carbon branching. The CPA compound according to the invention can exhibit a glass transition temperature (Tg) of at least about 185° C. to about 270° C.

15 Claims, 4 Drawing Sheets

SEM for example gas phase produced CPA

(56) References Cited

OTHER PUBLICATIONS

Akagi, K, et al., "Stereospecific Chlorination of Polyacetylene by Chemical Doping", Polymer, Elsevier Science Publishers B.V., GB, vol. 33, No. 19, Jan. 1, 1992, 4058-4065.

Catalado et al: "A Study of Chlorinated Polyacetylene", European Polymer Journel, Pergamon Press LTD. Oxford, GB, vol. 29, No. 12, Dec. 1, 1993, 1635-1639.

Akagi, K., Suezaki, M., and Shirakawa, H., Synthesis of Polyacetylene Films with High Density and High Mechanical Strength, Syn. Metals, 28 (1989) D1-D10.

Forte, L., Lien, M.H., Hopkison, A.C., and Bohme, D.K., Carbocationic Polymerization in the Gas Phase Polymerization of Acetylene Induced by BF2+, Can. J. Chem., 68 (1990), 1629-1635.

Cataldo, F., Acetylene Polymerization on Rh(1) Complexes, Polymer, 1992, v. 33, No. 14, p. 3073-3075.

Springborg, Michael, Structural and Electronic Properties of Fluorinated and Chlorinated Polyacetylene, J. Am. Chem. Soc., 1999, 121 (48), pp. 11211-11216.

Matnishyan, H.A., Akhnazaryan, T.L, Voskanyan, P.S., and Korshak, Yu.V., Preparation of Soluble Functional Polymers by Modification of Nano-sized Polyacetylene, Eur. Poly J., 2009, 45, pp. 1038-1045.

Lam, Jacky, and Tang, Ben Zhong, "Functional Polyacetylenes," Acc. Chem. Res., 2005, 38, 745-754.

Deits, Walter; Cukor, Peter; Rubner, Michael; and Jopson, Harriet, "Physical, Chemical, and Electrical Properties of Various Preparations of Polyacetylene," J. Electronic Materials, vol. 10, No. 4, 1981, 683-702.

Dickinson, L. Charles; Hirsch, Jacob A.; Karasz, Frank E.; and Chien, James C.W., "Polyacetylene Crystal Transformations during Thermal Isomerization," Macromolecules 1985, 18, 2374-2379.

Abadie, Marc J. M.; Hacene, Sidi M. Boukli; Cadene, Michel; and Rolland, Michel, "Effect of Polymerization Conditions on Polyacetylene Morphology," Polymer, 1986, vol. 27, December, 2003-2008.

* cited by examiner

Figure 1 – $^{13}$C NMR for Chlorinated Polyacetylene
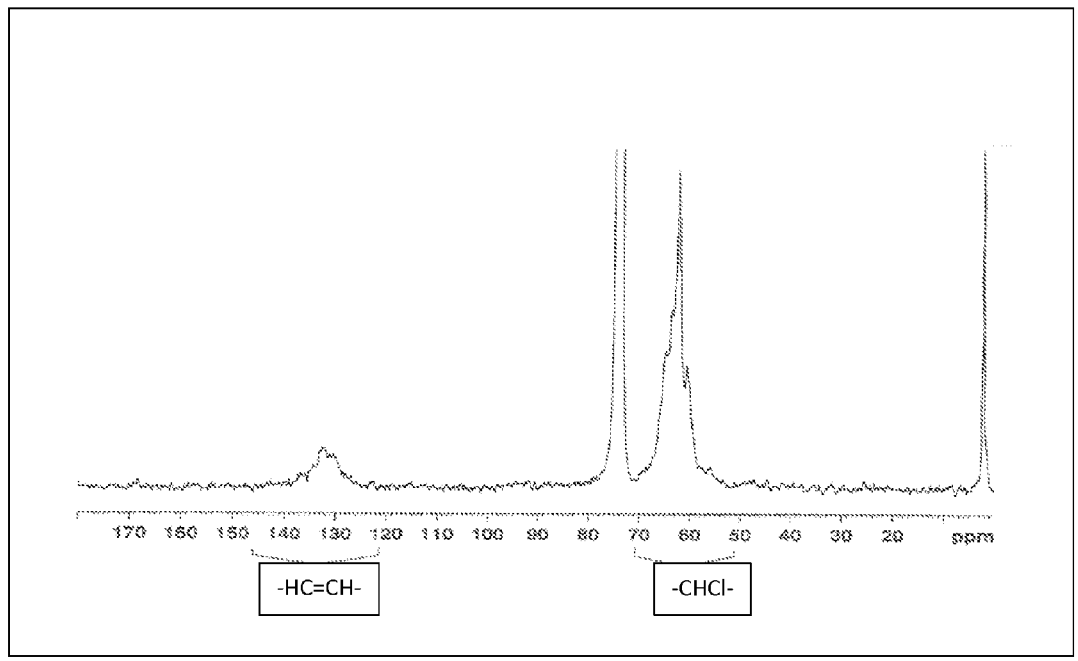
Figure 2 – $^{13}$C NMR for CPVC
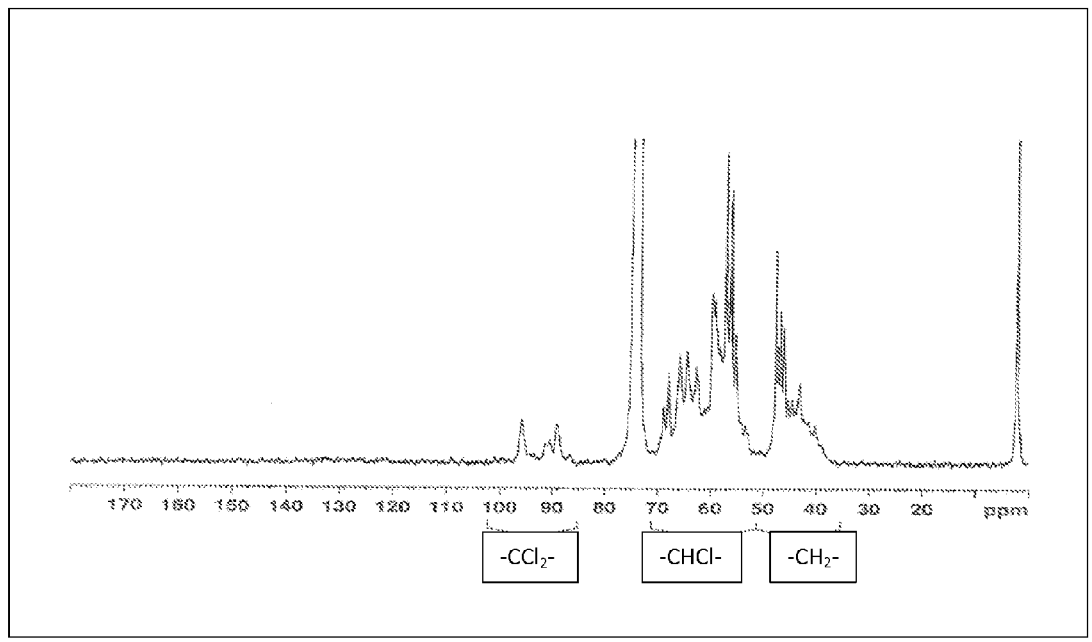

Figure 3 - $^{13}$C NMR for CPA made by slurry process in DMF
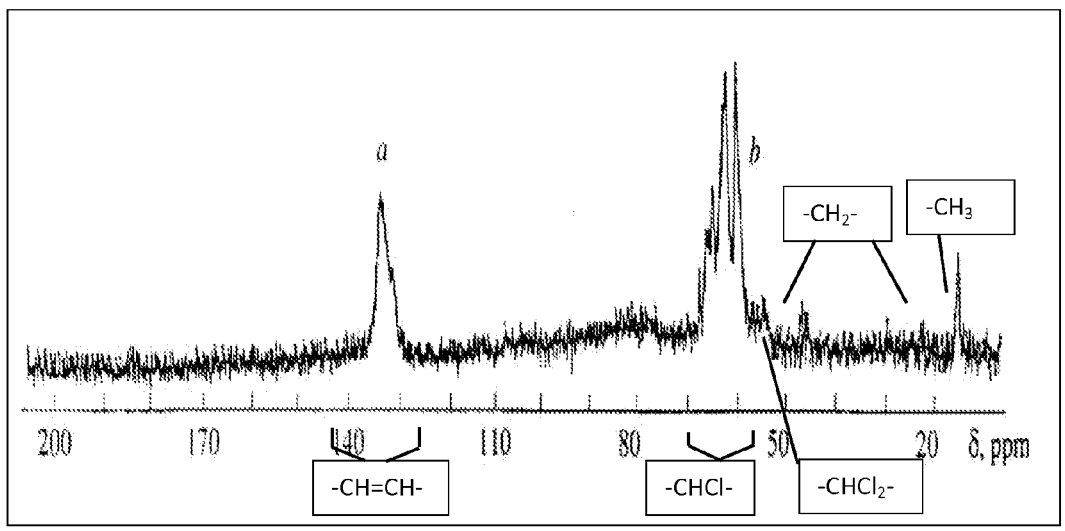
Figure 4. - FTIR for comparative example slurry produced CPA
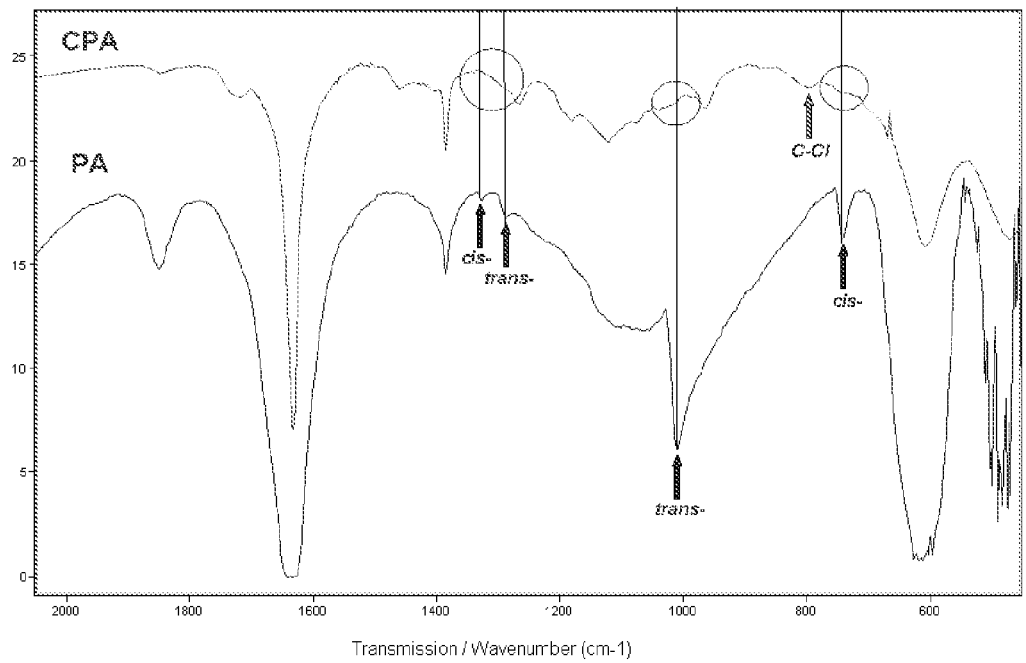

Figure 5. – FTIR for example gas phase produced CPA
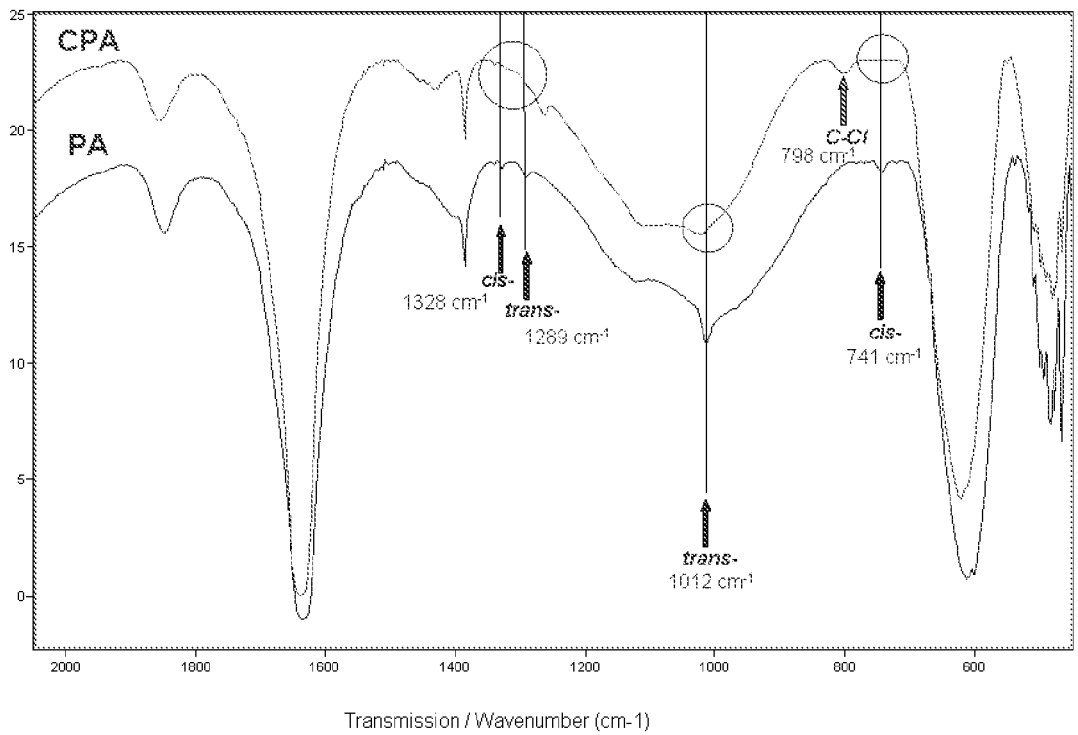
Figure 6. – SEM for comparative example slurry produced CPA
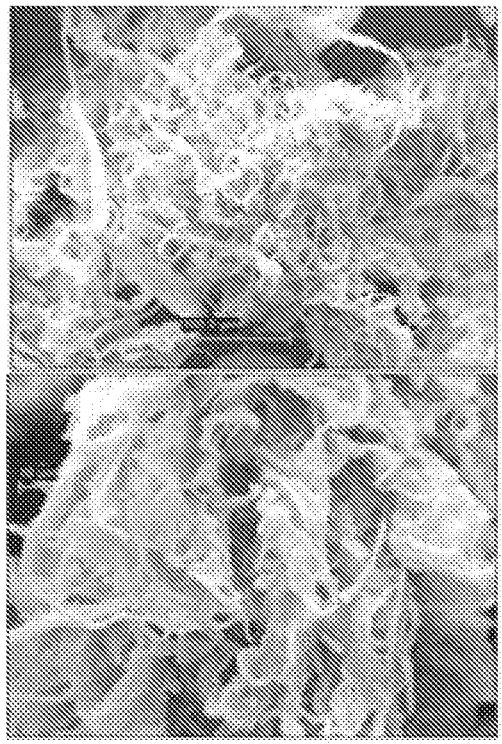

Figure 7. – SEM for example gas phase produced CPA
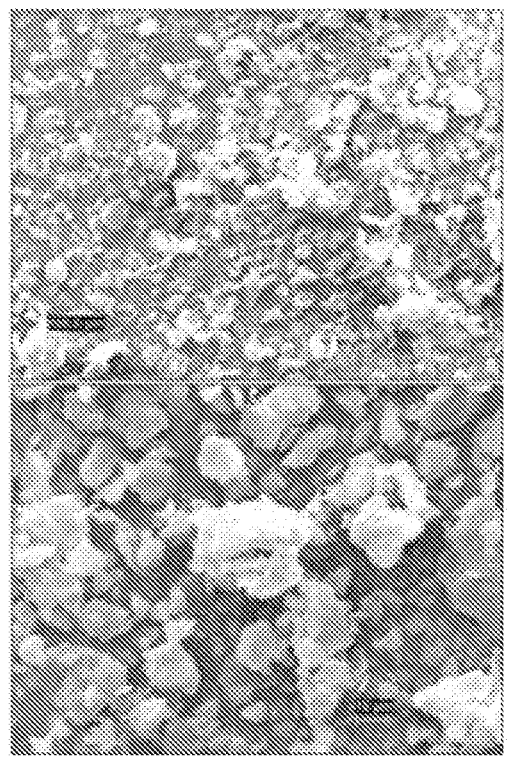

POLYACETYLENE AND CHLORINATED POLYACETYLENE AND PRODUCTION PROCESSES THEREOF

BACKGROUND OF THE INVENTION

The disclosed technology relates to polyacetylene and chlorinated polyacetylene (CPA). More particularly, the disclosed technology relates to a process for polymerizing acetylene to produce polyacetylene and the so-produced polyacetylene, as well as a further process to obtain CPA from the so-produced polyacetylene and the CPA product.

Polyacetylene is generally not prepared by polymerizing acetylene in the gas phase. Acetylene in pure form is an unstable highly flammable gas that uncontrollably oligomerizes at high concentrations. Samples of concentrated or pure acetylene can easily react in an addition-type reaction to form a number of products, typically benzene and/or vinyl acetylene. This reaction is exothermic. Consequently, acetylene can explode with extreme violence if the pressure of the gas exceeds about 200 kPa (29 psi). Thus, acetylene is usually handled as a solution. Solution polymerization of acetylene is impractical on an industrial scale.

Gas phase polymerization is an industrial polymerization method used with gaseous monomers such as ethylene, tetrafluoroethylene and vinyl chloride. In this process, the monomer is introduced under pressure of, for example, about 1.38 Mpa (200 psi) into a reaction vessel containing a polymerization initiator. The process may be performed as a heterogeneous or homogenous process. In a heterogeneous process, the polymerization initiator is a solid whereas in a homogeneous process the initiator is a gas. Once polymerization begins, monomer molecules diffuse to the polymer chains growing on the polymerization initiator. In the heterogeneous process, the resulting polymer is obtained as a granular solid. Heterogeneous gas phase polymerization presents technical challenges with regard to acetylene due to acetylene's unstable nature.

One reference, Akagi, K., Suezaki, M., and Shirakawa, H., Synthesis of Polyacetylene Films with High Density and High Mechanical Strength, *Syn. Metals*, 28 (1989) D1-D10, teaches a non-solvent method for preparing polyacetylene films. The method employs low temperatures and does not employ a supported catalyst or produce a bulk powder.

Similarly, Forte, L., Lien, M. H., Hopkison, A. C., and Bohme, D. K., Carbocationic polymerization in the gas phase polymerization of acetylene induced by $BF_2^+$, *Can. J. Chem.*, 68 (1990) 1629-1635, teaches a method for homogeneous gas phase polymerization of acetylene. The method employs ambient temperatures but does not employ a supported catalyst, produce a bulk powder, or produce true polyacetylene, i.e., a linear or substantially linear polymer consisting of repeat units equivalent to acetylene.

Another reference, Cataldo, F., Acetylene Polymerization on Rh(I) Complexes, *Polymer*, 1992, v. 33, No. 14, p. 3073-3075, teaches a solvent method to produce what is speculated to be linear polyacetylene films. The films produced are not characterized.

Due to the highly reactive nature of polyacetylene, most methods of characterization cause polyacetylene to react and change form. Thus, polyacetylene cannot be easily characterized. However, poly(di-functionalized acetylene) is very similar to polyacetylene. Because the difference between poly(di-functionalized acetylene) and polyacetylene is only two functional groups X, as shown below;

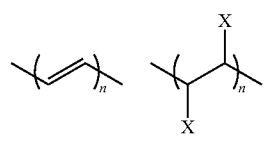

Polyacetylene  Functionalized polyacetylene properties, such as molecular weight and atomic structure can be easily deduced from the functionalized version.

One example of a poly(di-functionalized acetylene) employed for testing purposes can be poly(di-chlorinated acetylene). Poly(di-chlorinated acetylene) can be easily tested, for example, by GPC, $^{13}$C-NMR, FTIR, TGA, DSC and SEM analysis. Moreover, a symmetrically chlorinated polyacetylene could provide benefits over current chlorinated polymers, such as CPVC.

Chlorinated Poly(Vinyl Chloride) (CPVC) has many useful properties. It is environmentally friendly, corrosion, chemical, and flame resistant, easily processable and cost effectively producible.

Current CPVC production is performed by a slurry process in water. In this process, PVC water slurry is treated with chlorine in the presence of UV light to form CPVC as shown in Graphic 1, and the resulting CPVC goes further into a compounding process to make the final product.

Graphic 1. Current CPVC technology: slurry process in water

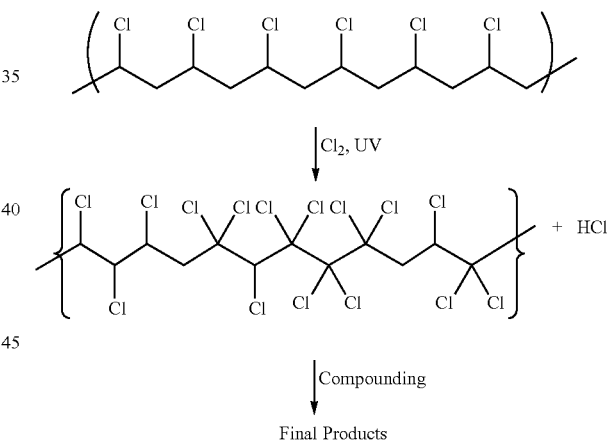

Despite the benefits of CPVC, the conventional slurry technique has many fundamental limitations, such as HCl generation after chlorination, compositional heterogeneity of the end product resulting in several different types of chlorinated segment units in the polymer backbone, a broad glass transition temperature range, a narrow processing temperature window, and strong dependence of raw material cost on volatile PVC price.

Poly(1,2-dichloroethylene) is a theorized but as yet unknown di-chlorinated polymer product in the CPVC family, differing from CPVC in its stereo-regularity as shown in Graphic 2. The polymer has long been thought of as the most attractive material within the CPVC family due to its theoretically excellent thermal properties. Poly[1,2-dichloroethylene] has been theorized to have a glass transition temperature (Tg) of about 270° C., much higher than the 155° C.

average Tg for CPVC produced today. Poly[1,2-dichloroethylene] is also theorized to have a much higher softening point.

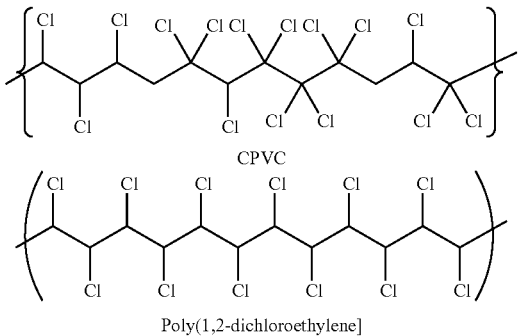

Example CPVC segment vs. Poly[1,2-dichloroethylene] segment

After over 30 years of pursuit, poly[1,2-dichloroethylene] has not been attainable by direct polymerization of 1,2-dichloroethylene monomers. Because polyacetylene is an insoluble polymer, researchers have reported on the chlorination of polyacetylene to impart solubility to the polyacetylene for purposes of characterization. However, chlorination of polyacetylene to produce poly[1,2-dichloroethylene] has never been reported.

U.S. Pat. No. 3,367,925 (issued Feb. 6, 1968 to Liu) teaches a method of polymerizing dichloroethylene. The product is called a symmetrical dichloroethylene polymer. However, the examples have not proven to be reproducible. Moreover, the product disclosed is not characterized in any manner, including by molecular weight or chlorine content.

Using a density-functional method, Springborg, Michael, *Structural and Electronic Properties of Fluorinated and Chlorinated Polyacetylene, J. Am. Chem. Soc.,* 1999, 121 (48), pp. 11211-11216, calculated the electronic and structural properties of several polymers, including a $(CCl)_x$ structure, which represents poly[1,2-dichloroethylene]. The computations were theoretical to determine structure and bonding, no samples were actually made.

Cataldo, Frank, *A Study of Chlorinated Polyacetylene, Eur. Poly. J.,* 1993, 29(12), pp. 1635-1639, chlorinated polyacetylene to obtain a polymer of poly[1,2-dichloroethylene] having disyndiotactic and atactic portions interspersed randomly by short polyacetylene segments, wherein the chlorinated polymer had a maximum chlorine content of 64 wt. % and a maximum decomposition rate at 170° C. Molecular weight was not reported.

Akagi, K., Kadokura, T., and Shirakawa, H., *Stereospecific Chlorination of Polyacetylene by Chemical Doping, Polymer,* 1992, 33(19), pp. 4058-4065 also teaches a chlorinated polyacetylene compound. However, neither the final chlorine content nor molecular weight is taught.

Matnishyan, H. A., Akhnazaryan, T. L., Voskanyan, P. S., and Korshak, Yu. V., *Preparation of Soluble Functional Polymers by Modification of Nano-sized Polyacetylene, Eur. Poly. J.,* 2009, 45, pp. 1038-1045, teaches chlorinated polyacetylene having molecular weights up to 123,000. However, the polymers were only chlorinated up to 72 mol % calculated on the number of CHCl units in relation to the number of carbon atoms in the polymer backbone. Moreover, this reference teaches that solvent-based chlorination of polyacetylene produced by conventional slurry-phase acetylene polymerization gives a chlorinated product with significant levels of $CH_2$ units (5-12 mole % by $^1H$ NMR and 0.4%-10.4% by FTIR).

Not only is an easier and more industrially ready process needed to produce polyacetylene, but a polyacetylene compound is needed that can allow the production of a high molecular weight, highly chlorinated, symmetrical polyacetylene approaching true poly(1,2-dichloroethylene).

SUMMARY OF THE INVENTION

In a first aspect of the invention, the inventors have discovered a process for polymerizing acetylene in a heterogeneous gas phase polymerization reaction that avoids the difficulties of previous methods.

Thus, in one embodiment, the invention provides a process of heterogeneous gas phase polymerization of acetylene to produce polyacetylene as a bulk powder.

In another embodiment, the invention provides polyacetylene characterized in that upon chlorination, the resultant chlorinated polyacetylene (CPA) is comprised primarily of repeat units equivalent to 1,2-dichloroethylene and repeat units equivalent to acetylene, as measured by $^{13}C$-NMR.

In a second aspect of the invention, the invention is directed to a CPA compound approaching true poly(1,2-dichloroethylene), comprised primarily of repeat units equivalent to 1,2-dichloroethylene and repeat units equivalent to acetylene, as measured by $^{13}C$-NMR.

In one embodiment, the invention provides a CPA compound exhibiting a Tg of at least 185° C. when chlorinated to a level of at least 67.3 wt % chlorine, and a weight average molecular weight (Mw) as measured by GPC of at least 30,000 g/mole.

In one embodiment, the invention is also directed to a process of directly producing a CPA compound in bulk powder formed by the gas phase polymerization of acetylene followed by gas phase chlorination of the resultant polyacetylene polymer.

BRIEF DESCRIPTION OF THE FIGURES

FIG. 1 is a $^{13}C$ NMR spectrum for a CPA compound made by a gas phase process.

FIG. 2 is a $^{13}C$ NMR spectrum for a comparative CPVC compound.

FIG. 3 is a $^{13}C$ NMR spectrum for a comparative CPA compound made by a slurry process in DMF.

FIG. 4 is an FTIR spectrum for a comparative example of a CPA compound made by a slurry process.

FIG. 5 is an FTIR spectrum for a CPA compound made by a fixed bed heterogeneous gas phase process according to one aspect of the invention.

FIG. 6 is an SEM photograph for a comparative example of a CPA compound made by a slurry process.

FIG. 7 is an SEM photograph for a CPA compound made by a fixed bed heterogeneous gas phase process according to one aspect of the invention.

DETAILED DESCRIPTION OF THE INVENTION

Various preferred features and embodiments will be described below by way of non-limiting illustration.

As used herein, a polymer comprising repeat units equivalent to 1,2-dichloroethylene means a polymer comprising repeat units as shown in formula I. As used herein, poly[1,2-dichloroethylene] means a polymer consisting essentially of repeat units equivalent to 1,2-dichloroethylene.

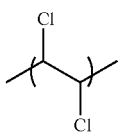

I

As used herein, a polymer comprising repeat units equivalent to acetylene means a polymer comprising repeat units as shown in formula II. As used herein, polyacetylene (PA) means a polymer consisting essentially of repeat units of formula II.

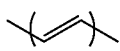

II

As used herein, CHCl means the unit as shown in formula III.

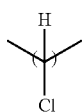

III

As used herein, CH2, CCl2, CCl, and CH3 mean, without being limited by specific stereochemistry, the units shown in formulas IV-VII, respectively, wherein "•" represent carbon-carbon bonds sufficient to fill the remaining valency of the carbon atom shown.

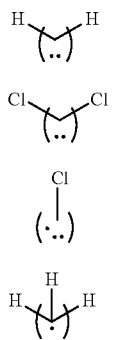

IV

V

VI

VII

As used herein, branching or carbon-carbon branching refers to the replacement of a substituent, e.g., a hydrogen atom, on an inner monomer subunit of the polymer backbone by another polymer chain having a carbon backbone.

As used herein, crosslinking or carbon-carbon crosslinking refers to carbon-carbon bonds that link one polymer chain to another, either by direct interaction of the backbones or through a branch. As used herein, crosslinking can be considered a form of branching.

As used herein, backbiting refers to the intramolecular termination of a polymerization reaction resulting in the formation of a cyclic oligomer. As used herein, backbiting can be considered a type of branching.

Branching and crosslinking may result from the formation of carbon-carbon or various other types of covalent bonds. While it is contemplated that some small amounts of impurities in the system could potentially cause some small amount of other branching or crosslinking to occur, when describing the percentage of branching and crosslinking herein it is meant the number of carbon atoms in the polymer backbone bonded to other carbon atoms not in the polymer backbone, divided by the total number of carbon atoms in the backbone.

As used herein, the term "linear" means the complete absence of branching, crosslinking and backbiting. As used herein, "substantially linear" may include compounds wherein the backbone has less than 1.0% (calculated by the number of branched monomer units divided by the total number of monomer units) branching and crosslinking, or less than 0.5% branching and crosslinking, or less than 0.01% branching and crosslinking.

In one aspect, the invention is directed to a method of directly producing a bulk powder form of polyacetylene by a process of gas phase polymerization of acetylene.

Gas phase polymerization of acetylene can be carried out by (a) providing a reactor having a reaction chamber, (b) providing within the reaction chamber a polymerization initiator and a gaseous atmosphere inert to acetylene, (c) providing a source of gaseous acetylene having a substantial absence of solvent into the inert atmosphere within the reaction chamber, and (d) maintaining the reaction chamber at a polymerization promoting temperature and pressure for a residence time sufficient to allow the gaseous acetylene to polymerize into polyacetylene.

The reactor for the gas phase polymerization of acetylene can be any type of reactor suitable for gaseous reactions. Specific examples of suitable reactors include fixed bed reactors, fluidized bed reactors, and stirred bed reactors.

When designing the reactor chamber, generally the reactor chamber providing better diffusion will be more desirable. The better diffusion through the reactor, the higher the chances acetylene monomer will make contact with the polymerization initiator, propagating polymerization. Of course, depending on the desired properties of the final polyacetylene product, reactor chambers having various diffusion rates may be employed.

Due to the highly reactive nature of acetylene, the reaction chamber of the reactor can be filled with an inert atmosphere to prevent unwanted side reactions, such as oxidation reactions. Some types of inert gaseous atmospheres suitable for the process include highly pure nitrogen and argon gas. The reaction chamber also may be fully evacuated of all gaseous atmosphere prior to introduction of acetylene monomer gas such that acetylene monomer gas is the only gas present during the reaction.

The gas phase polymerization of the present invention is a heterogeneous process. By "heterogeneous" it is meant that gaseous acetylene polymerizes on a solid catalyst.

Solid catalysts suitable for the present invention can comprise transition metals (elements in groups 3 to 12 on the periodic table), such as, for example, titanium, nickel and rhodium. The catalyst may or may not be supported. Suitable supports can comprise alkali metals (group 1 elements on the periodic table), alkaline earth metals (group 2 elements on the periodic table) or an element on the periodic table from groups 13-16. Example supports can be magnesium and silicon. The transition metal solid catalyst may be a pre-catalyst that can be activated by a post-transition metal (Al, Ga, In, Sn, Tl, Pb, Bi), such as, for example, aluminum.

In one embodiment, the polymerization can employ a traditional solid supported catalyst, such as a Ziegler Natta type catalyst. For example, the solid catalyst may be a solid supported catalyst based on titanium compounds or a metallocene catalyst. In one embodiment, the catalyst employed can be a solid supported catalyst based on titanium compounds.

In one embodiment, the solid supported catalyst comprises a titanium pre-catalyst. Titanium compounds suitable for the present invention as a pre-catalyst can include titanium alkoxide or titanium halide compounds having the formula $TiX_4$, where X is OR, or a halogen, such as Cl, Br, or F, and where R can be any alkyl group of from 1 to 32 carbon atoms. Examples of titanium alkoxide compounds of the present embodiment include titanium n-butoxide ($Ti(OBu^n)_4$) and titanium isopropoxide ($Ti(OPr^i)_4$).

In one embodiment, the solid supported catalyst comprising a titanium compound may be activated by an organoaluminum activating compound, either before or after the titanium compound is supported on a solid support. Examples of organoaluminum activating compounds can include organoaluminum compounds having the formula $AlR_xCl_{(3-x)}$, or the formula $Al(R)_3$, wherein R can be any alkyl group of from 1 to 32 carbon atoms and x can be 1-3. Activation can occur by reacting the titanium compound with the organoaluminum activating compound in a solvent solution, such as hexane. The solvent solution can later be evaporated.

Solid supports can include, for example, $MgCl_2$, silica, alumina, silica-aluminas, zeolites and clays. The catalyst precursor may be impregnated on the solid support by methods known in the art, such as solution impregnation and incipient wetness impregnation. In solution impregnation, a suspension of the solid support is treated with a solution of the pre-catalyst (e.g., titanium alkoxide), and the resulting material is then activated (e.g., by organoaluminum compound) under conditions that will convert the pre-catalyst (often a metal salt) to a more active state. In the incipient wetness method, the active metal precatalyst is dissolved in an aqueous or organic solution. Then the metal-containing solution is added to a catalyst support containing the same pore volume as the volume of solution that was added. Capillary action draws the solution into the pores. The catalyst can then be dried and calcined to drive off the volatile components within the solution, depositing the metal on the catalyst surface.

Examples of specific solid supported catalysts contemplated within the present invention include $Ti(OBu^n)_4/MgCl_2$—$AlEt_3$, and $Ti(OBu^n)_4/SiO_2$—$Al(Bu^i_3)$. In certain circumstances, the catalyst can agglomerate during processing. The inventors have found that a co-catalyst system of triethylaluminum (TEAL or $AlEt_3$) and methylaluminoxane (MAO or $(Al(CH_3)O)_n$) as the activator can minimize agglomeration and provide desirable catalytic activity. Thus, in another embodiment, the solid supported catalyst can comprise $Ti(OBu^n)_4/MgCl_2$—$(AlEt_3)/((Al(CH_3)O)_n)$.

It has been found by the inventors that the ratio of activating compound to pre-catalyst can affect the form of the product. At ratios of activating compound to pre-catalyst of above 1, i.e., more activating compound present than pre-catalyst, it has been discovered that branching of the polymer occurs more prevalently. At ratios below 1, i.e., more pre-catalyst present than activating compound, it has been discovered that branching in the final polymer product could be minimized or completely eliminated, and that higher molecular weight polymerizations can be completed.

Without wishing to be bound by theory, it is contemplated that a lower activating compound to pre-catalyst ratio helps to ensure that only specific sites on the pre-catalyst are active for polymerization, thereby deterring an excess of polymer chains from initiating and interacting.

Accordingly, in one embodiment, the activating compound may be employed such that the solid supported catalyst exhibits activating compound to pre-catalyst ratios of between about 4/1 to about 1, or from about 3/1 to about 1, or between about 2/1 and about 1. In an alternate embodiment, the activating compound may be employed such that the solid supported catalyst exhibits activating compound to pre-catalyst ratios between about ¼ and about 1, or between about ⅓ and about 1, or about ½ and about 1.

In one particular embodiment, it has been found that solid supported catalysts comprising an organoaluminum activating compound and a titanium alkoxide pre-catalyst, such as, for example, $Ti(OBu^n)_4/MgCl_2$—$AlEt_3$, and $Ti(OBu^n)_4/SiO_2$—$Al(Bu^i_3)$, having a ratio of aluminum to titanium (Al:Ti) of between about ¼ and about 1, or about ⅓ and about 1 can produce polyacetylene having carbon-carbon branching and carbon-carbon crosslinking of less than 5%, or less than 3%, or less than 1%, and in some embodiments, can produce completely un-branched polyacetylene.

In another embodiment, the organoaluminum activating compound may be employed such that the catalyst exhibits a ratio of Al/Ti of about 4/1, 3/1, 2/1 or 1 and produces polyacetylene having greater than 5% up to a completely branched or cross-linked product, i.e., wherein every carbon atom in the polyacetylene can be branched.

The polymerization reaction can be started within a wide polymerization promoting temperature range. The polymerization promoting temperature for the reaction bed in the process of the invention can start at from about 40° F. (about 4.4° C.) to about 120° F. (about 48.9° C.). In certain embodiments, the temperature can start at from about 50° F. to about 115° F., or from about 60° F. to about 110° F., or from about 70° F. to about 105° F. In some embodiments, the reaction can be started at about 80° F., 90° F. or 100° F. It is expected that the polymerization reaction will cause the temperature within the reactor to rise from the starting polymerization promoting temperature.

The polymerization reaction also can be performed at a polymerization promoting pressure. Preferably the reaction is performed at about atmospheric pressure, that is, the atmospheric pressure at the reactor location. However, a slight vacuum may be applied. Further, given acetylene's instability and explosiveness under pressure, the polymerization promoting pressure should remain below 15 psig. Thus, the polymerization promoting pressure, in one embodiment, can be from about 0.0 psig to about 15 psig, or from about 0.5 psig to about 10 psig, or from about 1 to about 5 psig.

The residence time for the polymerization reaction can vary. Generally, when the temperature of the reaction levels off, it can be one indication that the polymerization reaction is complete. While the polymerization reaction may be left to react for days, the reaction can be completed in about 1 to about 3 hours.

Preferably, the polymerization occurs in the complete absence of solvent. However, acetylene is generally provided in a solvent, such as acetone. Thus, in one embodiment the polymerization occurs in the substantial absence of solvent. As used herein, substantial absence of solvent means that the polymerization may occur with trace amounts of solvent residual from the supplied acetylene at levels corresponding to the limitations of solvent removal processes known in the art.

In certain embodiments, the reactor may include water and acetone scrubbing systems. For example, a high capacity molecular sieve tower, cold trap, active carbon trap and combinations thereof may be added to the feed stream to increase the purity of the acetylene monomer feed.

The polyacetylene product may be used as is with the residual catalyst or the product may be purified in further steps, such as through removal of the catalyst by any of the procedures known to those skilled in the art (e.g., water washing).

In addition, the polyacetylene product can be further processed to add functional groups at the ethylenically unsaturated carbons. Functionalization of the polyacetylene can be achieved in one embodiment by reacting the polyacetylene in an atmosphere of the functional compound. The functionalization reaction can be completed in a gaseous atmosphere, in a liquid bath, or in a combination of both. Preferably the functionalization reaction is completed in a gaseous atmosphere by introducing the polyacetylene into an evacuated and clean reactor chamber and pumping in the functionalizing compound as a gas.

The functionalization reaction can be performed at a broad range of temperature and pressure. Similar to the gas phase production of polyacetylene, gas phase functionalization can be performed within a wide functionalization promoting temperature range. The functionalization promoting temperature for polyacetylene can be from about −40° F. (−40° C.) to about 250° F. (about 121.1° C.). In certain embodiments, the temperature can be from about 0° F. to about 200° F., or from about 20° F. to about 150° F. In a preferred embodiment, the functionalization promoting temperature can be from about 40° F. to about 100° F. In a preferred embodiment, the functionalization can be performed at ambient temperature.

The functionalization reaction also can be performed at a functionalization promoting pressure. For the sake of ease and cost efficiency, the functionalization is preferably performed at about atmospheric pressure. As with the polymerization, a slight vacuum may also be applied. It is to be appreciated that the higher the pressure in the reactor the greater the functionalization reactivity.

The residence time for the functionalization reaction can vary. Generally, when the temperature of the functionalization levels off, it can be one indication that the functionalization is complete. While the functionalization may be left to react for days, the functionalization reaction can be completed in about 1 to about 3 hours.

Functionalization may also be by soaking the polyacetylene in a liquid bath of the functionalizing material. Liquid bath functionalization may be a pre-treatment, post-treatment or alternative to gas phase functionalization.

In one embodiment, a CPA compound can be produced by chlorinating a polyacetylene polymer. For example, polyacetylene polymer can be chlorinated in the gas-phase, followed by post-treating the chlorinated product in a liquid chlorine bath for about 2 hours to about 1 day.

The above described process can produce true polyacetylene polymer and a poly[1,2-di-functionalized-acetylene] polymer. True polyacetylene polymer consists of a long chain of carbon atoms structured in alternating CH double bond units. Schematically, true polyacetylene can be exemplified by the repeat units in formulas A and B or mixtures thereof, where the repeat units in A represents the trans-isomer and the repeat units in B represents the cis-isomer.

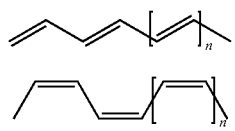

A

B

The number of monomer units, n, of the polyacetylene compound produced will be sufficiently high for the compound to be considered a polymer, as opposed to an oligomer. Generally, n is greater than 10 for a compound to be considered a polymer. In the polyacetylene compound of the present embodiment, n can be greater than 10, and preferably can be 50 or greater, 75 or greater, or 100 or greater. In one embodiment, n can be 300 or greater, 500 or greater, 1000 or greater, or n can be 1500 or greater.

In a preferred embodiment, the polyacetylene can be characterized by being completely free of solvent. In another embodiment, the polyacetylene can be substantially free of solvent. In further embodiments, the polyacetylene can be linear, or substantially linear.

Polyacetylene, like the precursor acetylene, can be highly reactive. As such, most methods of characterizing the polyacetylene cause it to react and change form. Thus, polyacetylene cannot be easily characterized. However, poly(di-functionalized acetylene) is very similar to polyacetylene. Because the difference between poly(di-functionalized acetylene) and polyacetylene is only two functional groups X, as shown below;

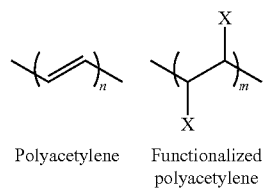

Polyacetylene    Functionalized polyacetylene properties, such as molecular weight and atomic structure can be easily deduced from the functionalized version.

One example of a poly(di-functionalized acetylene) employed for characterizing purposes can be poly(di-chlorinated acetylene) (CPA). CPA can be easily characterized, for example, by GPC, $^{13}$C-NMR, FTIR, XRD, and SEM analysis.

CPA according to one aspect of the invention comprises repeat units equivalent to 1,2-dichloroethylene, as shown in formula I, or repeating units of formula I along with repeat units equivalent to acetylene of formula II.

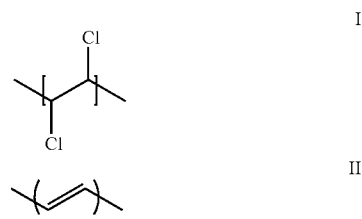

As used herein, the term CPA or CPA compound refers to a polymer of either repeating units of formula I or repeating units of formula I and formula II. CPA compound according to the invention containing primarily repeat units equivalent to 1,2-dichloroethylene and repeat units equivalent to acetylene is indicative that the precursor PA was true PA consisting essentially of repeat units equivalent to acetylene. By "primarily" repeat units equivalent to 1,2-dichloroethylene and repeat units equivalent to acetylene, it is meant that only units of CHCl and units equivalent to acetylene are detectable within the detection limits of $^{13}$C NMR. $^{13}$C NMR can generally detect elements present at about 5 mole % or more, or 4 mole % or more, and often 3 mole % or more, or even 2 mole % or more and sometimes even 1 mole % or more. Thus, "primarily" means that the primary component(s) are present in a sum amount of about 95 mole % or greater, or 96 mole % or greater, or 97 mole % or greater. Preferably, the primary component(s) will be present in a sum amount of about 98 mole % or greater and most preferably about 99 mole % or greater. PA and CPA as contemplated herein contain less than 5 mole %, or 4 mole % or 3 mole %, and in some cases less than 2 mole %, and preferably less than 1 mole % of any repeat units of CCl, CCl$_2$, CH$_2$, CH$_3$ or any other units besides repeat units equivalent to 1,2-dichloroethylene and repeat units equivalent to acetylene.

As a copolymer, the CPA compound may be an alternating, periodic, statistical, random, or block copolymer. In one embodiment, the CPA compound can be a random or block copolymer having a mole ratio as determined by $^{13}$C-NMR of units equivalent to acetylene to units of CHCl of about 1:6 to about 1:12. In one embodiment, the CPA compound can have a ratio of units equivalent to acetylene to units of CHCl of about 1:7 to about 1:11, or about 1:8 to about 1:10. As a copolymer, the CPA compound can comprise about 75 mol % CHCl (% of carbons in backbone which are CHCl), or about 80 mol % CHCl. In one embodiment, the CPA compound can comprise greater than 85 mol % CHCl or even greater than 90 mol % CHCl. Notably, $^{13}$C-NMR can detect carbon-carbon double bonds and carbon-chlorine bonds. Thus, the mole ratio of units equivalent to acetylene to units of CHCl, as well as the mol % of CHCl can easily be determined from the $^{13}$C-NMR spectrum.

The Mw of the CPA compound, as determined by GPC in THF solvent, can be about 1000 or greater, or about 10,000 or greater, or 30,000 or greater or 60,000 or greater, or 100,000 or greater. The CPA may also have a polydispersity (Mw/Mn) of between about 1 and 6, or greater than 1, or greater than 2, or greater than 3. In some embodiments, the polydispersity can be greater than 3.5 or greater than 4. Polydispersity refers to the Mw divided by the number average molecular weight, Mn.

Given that primarily units of 1,2-dichloroethylene and units equivalent to acetylene can be present in the CPA as contemplated herein, the molecular weight of PA produced according to the inventive process can be deduced from GPC analysis of a CPA sample. Thus, polyacetylene as produced according to the inventive process may have an Mw of greater than about 130, or 200 or 2000, and in some cases greater than 3000, or even greater than 4000. Preferably, the polyacetylene has a Mw of greater than 5000, 6000, 7000, or even 8000.

The CPA compound can comprise greater than 67.3 wt % chlorine, or even greater than 67.5 wt %, or greater than 68 wt % chlorine. In certain embodiments, the chlorine content of the CPA compound can be between about 67.3 wt % and about 73.14 wt % of the compound, or between about 67.5 wt % and about 73.14 wt % of the compound, or between about 68 wt % and about 73.14 wt % of the compound, or about 69 wt % and about 73.14 wt % of the compound. In one embodiment, the chlorine content can be about 70.0 wt % of the CPA compound.

The CPA compound can be linear, or substantially linear.

The CPA compound, and thus, the PA compound, can be characterized, for example, through $^{13}$C-NMR and FTIR testing. $^{13}$C-NMR provides a determination of the ratio of CHCl to units equivalent to acetylene, % unsaturation present and % Cl present. By employing an inverse-gated-decoupling sequence, quantitative 1H decoupled $^{13}$C spectra can be obtained, thereby allowing the mole % of each species discovered on the NMR spectrum to be obtained by standard integration of the peaks. FTIR can provide evidence for the presence of cis (1328 cm$^{-1}$ and 741 cm$^{-1}$) and trans (1289 cm$^{-1}$ and 798 cm$^{-1}$) acetylene units in polyacetylene, which disappear upon chlorination and are replaced by a CHCl peak (at 798 cm$^{-1}$).

FIG. 1 shows a typical $^{13}$C NMR analysis obtained employing a 200 MHz Bruker AV spectrometer, with overnight acquisition and an inverse-gated-proton-decoupling pulse sequence at about a 5 second repetition rate for a CPA product produced in the gas phase process, as measured in a tetra-chloroethane-d2 solvent to a detection limit of 1 mole %. One of ordinary skill in the art would recognize that the peak with a maximum at about 132 ppm represents an unsaturated CH=CH bond in the measured product. Likewise, it would be recognized that the peak having a maximum at about 62 ppm is due to the presence of CHCl in the product. The peak at 75 ppm also would be recognized to be due to the solvent used in the NMR analysis (tetra-chloroethane-d2) and the peak to the far right due to an internal reference used for calibration. Given that primarily acetylene units and CHCl units are present in the CPA compound, it can be inferred that the underlying polyacetylene product was true linear polyacetylene.

For sake of comparison, FIG. 2 shows a typical $^{13}$C NMR analysis, also employing an inverse-gated-decoupling sequence, for CPVC. The analysis for a typical CPVC polymer shows the presence of CCl$_2$ units (at between about 85-102 ppm), CHCl units (at between about 52-72 ppm), and CH$_2$ units (35-52 ppm).

For further comparison, FIG. 3 shows a $^{13}$C NMR analysis for a CPA compound made by a slurry process in DMF, as published in *Eur. Poly. J.*, 2009, 45, p 1041. The author teaches the presence of CHCl$_2$ units (at about 55 ppm), CHCl units (at between about 67.3-60.0 ppm), CH$_3$ units (at between about 16.5-14 ppm) and CH$_2$ units (at between about 45-22 ppm).

A comparison of the figures provides a clear difference between standard CPVC, slurry produced CPA, and CPA produced according to the gas phase process; namely a lack of anything but repeat units equivalent to acetylene and CHCl units in the chlorinated polyacetylene made in the gas phase process.

The CPA compound of this invention can be characterized by a glass transition temperature (Tg) of greater than 134.5° C. to about 270° C., or from about 150° C. to about 270° C., or from about 175° C. to about 270° C. or from about 200° C. to about 270° C., 270° C. being the theoretical Tg for true poly[1,2-dichloroethylene]. In one embodiment, the CPA compound has a Tg of greater than about 165° C., or greater than about 185° C., or greater than about 200° C.

The morphology of the PA and CPA produced can be deduced from SEM analysis of poly(di-chlorinated acetylene). PA and CPA produced according to one aspect of the invention exhibit a dense powdery morphology.

The CPA polymer of formula I can be completely free of solvent or substantially free of solvent. Substantially free of solvent means that the CPA compound contains only trace amounts of solvent residual from the starting materials as supplied, for example, at levels corresponding to the limitations of solvent removal processes known in the art.

EXAMPLES

Example 1

Heterogeneous MgCl$_2$-Supported Alkyl Titanate Pre-Catalyst

A supported alkyl titanate compound is prepared according to Soga, K; Miyoshi, K; Inoue, N. *Synthetic Metals* 1988, 24, 239-244 using Ti(OBu")$_4$ and MgCl$_2$ as support. This compound is activated with Al(Et)$_3$.

Comparative Example 1

The catalyst prepared in Example 1 is used to polymerize acetylene in slurry phase according to the method described in Soga, K; Miyoshi, K; Inoue, N. *Synthetic Metals* 1988, 24, 239, using toluene as solvent. The black resulting polymer gave an infrared spectrum consistent with a mixture of cis- and trans-polyacetylene (FIG. 4). This polymer was subsequently chlorinated according to the procedure described in Natta, G; Mazzanti, G; Corradini, P. *Atti Accad. Naz. Lincei, Rend. Classe Sci. Fis. Mat. Nat.* 1958, 25, 3; and Cataldo, F. *Eur. Polym. J.* 1993, 29, 1635 to give a whitish solid product. This material gave an infrared spectrum consistent with poly (di-chlorinated acetylene) (FIG. 4). The catalyst after Al(Et)$_3$ activation had a molar Al:Ti ratio of 5.5.

For the FTIR, attenuated total reflectance (ATR) spectra were acquired on the Nicolet Nexus 670 Fourier Transform Infrared (FT-IR) spectrometer, at 4 cm$^{-1}$ resolution (at least 1 data point every 2 cm$^{-1}$), using Happ-Genzel apodization with no zero-filling, collecting 200 co-added scans each for the background and sample spectra. The specific ATR accessory was a Pike MIRacle™ (available from Pike Technologies) which was equipped with a single-bounce, 45°-incidence angle germanium crystal. The background spectrum was collected from the clean, sample-free ATR crystal. For the sample spectrum, a small amount of the sample powder was placed on the surface of the ATR crystal and a vendor-supplied clamp was used to press the sample into intimate contact with the crystal; this clamp uses a pressure-sensitive slip clutch so that the same nominal clamp pressure is applied to every sample. After the spectra had been acquired, the FT-IR data system was used to indicate the positions of the peaks of interest.

The slurry prepared material exhibited a fibrous morphology as shown in FIG. 6, and exhibited the properties shown in Table 1.

TABLE 1

| | |
|---|---|
| Tg ° C. | 182 |
| T$_{decomp}$ ° C. | 280 |
| % Unsaturated C, $^{13}$C-NMR | 21 |
| Wt. % Cl (theoretical) | 63.3 |
| % Chlorination | ~60 |

Example 2

Fixed Bed Gas Phase Process

The catalyst from Example 1 (1.2 g, 1.0 mmol of Ti) is dusted onto glass wool, activated with Al(Et)$_3$ (0.33 g, 2.93 mmol), and the resulting mixture placed inside a 500 mL resin kettle reactor under a N$_2$ atmosphere. The reactor is then charged with 1 atm of filtered and purified acetylene from a tank of acetylene dissolved in acetone (Matheson Gas). The resulting black solid gives an infrared spectrum consistent with a mixture of cis- and trans-polyacetylene (FIG. 5). The reactor is evacuated and then charged with 1 atm of chlorine gas, which results in conversion of the black solid to a white solid, which gives infrared spectrum consistent with poly(di-chlorinated acetylene) (FIG. 5).

The poly(di-chlorinated acetylene) produced exhibits a dense powdery morphology as shown in FIG. 7, and the properties shown in Table 2.

TABLE 2

| | |
|---|---|
| Tg ° C. | 180 |
| T$_{decomp}$ ° C. | 304 |
| % Unsaturated C, NMR | 16 |
| Wt. % Cl | 52.1 |
| % Chlorination | ~40 |

Examples 3-9

Preparation of Catalyst

A Ti(n-Butoxide)$_4$ compound is activated by reacting it with an organoaluminum activating compound in a hexane solution. The solution is then impregnated into a pre-treated support to incipient wetness and the hexane is evaporated. The final active catalyst, which is a supported Ziegler-Natta catalyst, is a dry free-flowing powder.

Polymerization

The polymerization of acetylene is conducted at atmospheric pressure by fluidizing the catalyst with nitrogen or argon, and then feeding a controlled amount of purified acetylene gas into the fluidizing gas. The fluidizing bed temperature is monitored and the reaction rate is controlled by adjusting the amount of acetylene present in the gas mixture. The polymerization is conducted for 3 hours, at which time the acetylene feed is stopped. The inert fluidizing gas is continued for a time to purge out any remaining acetylene. Visual observation of the fluidizing bed during the reaction showed that the catalyst turned the characteristic black color of polyacetylene within a few minutes of initiating acetylene feed.

Chlorination

The chlorination of the polyacetylene is conducted at atmospheric pressure by fluidizing the reaction product (polyacetylene still on the catalyst support) with nitrogen or argon, and then feeding a controlled amount of chlorine gas into the fluidizing gas. The fluidizing bed temperature is monitored and the reaction rate is controlled by adjusting the amount of chlorine present in the gas mixture. As the reaction continues, the supported polymer turns from black to white at which time the reaction rate drops off quickly. As the reaction rate decreases, the chlorine feed is gradually increased to 100% and maintained until the bed temperature has fallen to room temperature. The chlorine feed is then stopped and the chlorinated polyacetylene is fluidized with inert gas to purge out any remaining chlorine gas. The CPA is then separated from the silica support by first pouring the mixture into deionized water to neutralize any catalyst residuals, drying in a vacuum oven, and then pouring into THF (tetrahydrofuran) to dissolve the CPA, and filtering out the solids. The CPA is then precipitated with MeOH (methanol) and vacuum oven dried.

Chlorine content of the polymer is determined by $^{13}$C-NMR. Further increase in chlorine content is achieved by reacting the recovered CPA with liquid chlorine at −76° C. for 3 hours.

Results

| Te☐ | Ex. 3 | Ex. 4 | Ex. 5 | Ex. 6 | Ex. 7 | Ex. 8 | Ex. 9 |
|---|---|---|---|---|---|---|---|
| Wt % Cl (NMR) | 70.0 | 68.0 | 68.1 | 69.3 | 68.0 | 67.4 | 66.7 |
| (CHCl/HC=CH) | 11.6 | 7.0 | 7.1 | 9.6 | 7.0 | 6.2 | 5.5 |
| Mol % CHCl | 92.06 | 87.50% | 87.65% | 90.57 | 87.50% | 86.11% | 84.62% |
| DSC (Tg) | 203.7 | 174.9 | 187.0 | 188.7 | 141.0 | 188.2 | 191.8 |
| Rx (Al/Ti) | 0.27 | 0.30 | 0.22 | 0.244 | 0.244 | 0.325 | 0.27 |
| (Rx Temp (F.)) | (90-110) | (85-105) | (78-90) | (77-120) | (77-120) | (78-83) | |
| Max Temp | 113 F. | 119 F. | 93 F. | 126 F. | 126 F. | 100 F. | |
| GPC | | | | | | | |
| Mw | 39718 | 30446 | 67566 | 33791 | 4065 | 33996 | 69155 |
| Mn | 9661 | 7183 | 9157 | 7243 | 1911 | 6208 | 11774 |
| Mp | 9837 | 9093 | 8016 | 8325 | 2200 | 7003 | 10643 |
| Mw/Mn | 4.11 | 4.24 | 7.38 | 4.67 | 2.13 | 5.48 | 5.87 |

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

Each of the documents referred to above is incorporated herein by reference. The mention of any document is not an admission that such document qualifies as prior art or constitutes the general knowledge of the skilled person in any jurisdiction. Except in the Examples, or where otherwise explicitly indicated, all numerical quantities in this description specifying amounts of materials, reaction conditions, molecular weights, number of carbon atoms, and the like, are to be understood as modified by the word "about". It is to be understood that the upper and lower amount, range, and ratio limits set forth herein may be independently combined. Similarly, the ranges and amounts for each element of the invention can be used together with ranges or amounts for any of the other elements.

What is claimed is:

1. A polymer composition comprising polyacetylene of formula $(C_2H_2)_n$ wherein n is greater than 10, and wherein the polymer composition is in the form of a granular solid and has a polydispersity of greater than 3.5.

2. A process of producing the polymer composition according to claim 1 comprising a gas phase polymerization of acetylene in the presence of a supported catalyst.

3. The process of claim 2 wherein the supported catalyst comprises a solid support, a titanium alkoxide pre-catalyst, and an organoaluminum activating compound.

4. The process of claim 2 wherein the process is started at a temperature of between about 40° F. and 120° F.

5. The process of claim 2 wherein the process is started at atmospheric pressure.

6. The process of claim 2 wherein the catalyst is $Ti(OBu'')_4/MgCl_2$—$AlEt_3$.

7. The process of claim 2 wherein the catalyst is $Ti(OBu'')_4/SiO_2$—$Al(Bu^i_3)$.

8. The process of claim 2 wherein the catalyst is prepared having an Al/Ti ratio of from about 1/4 to about 1.0.

9. The process of claim 2, further comprising the additional step of functionalization in a gaseous atmosphere of a functional compound.

10. Chlorinated polyacetylene (CPA) comprised primarily of repeat units equivalent to 1,2-dichloroethylene and repeat units equivalent to acetylene, wherein the CPA is in the form of a granular solid and has an Mw as measured by GPC of at least 30,000 g/mole.

11. CPA according to claim 10 chlorinated to a level of at least 67.3 wt % chlorine.

12. CPA according to claim 10 exhibiting a Tg of at least 185° C.

13. A process for producing the composition of claim 10 comprising gas phase polymerization of acetylene to produce polyacetylene followed by chlorination of the polyacetylene.

14. The process of claim 13 wherein the chlorination comprises a gas phase chlorination.

15. The process of claim 13 wherein the chlorination comprises chlorination in a liquid chlorine bath.

* * * * *